United States Patent [19]

Eiglmeier

[11] 4,082,807

[45] Apr. 4, 1978

[54] PROCESS FOR THE MANUFACTURE OF AROMATIC 1,3-DIKETONES

[75] Inventor: Kurt Eiglmeier, Idstein, Taunus, Germany

[73] Assignee: Hoechst Aktiengesellschaft, Frankfurt am Main, Germany

[21] Appl. No.: 600,207

[22] Filed: Jul. 30, 1975

Related U.S. Application Data

[62] Division of Ser. No. 491,476, Jul. 22, 1974, Pat. No. 3,937,737.

[30] Foreign Application Priority Data

Jul. 23, 1973 Germany .............................. 2337396

[51] Int. Cl.$^2$ .............................................. C07C 49/76
[52] U.S. Cl. .......................... 260/590 R; 260/590 FA; 260/590 FB; 260/590 D; 260/590 E; 260/347.8; 260/340.7; 260/332.3 R; 260/479 R; 560/139; 560/138; 560/142; 560/145; 560/144
[58] Field of Search .................. 260/590, 340.7, 347.8, 260/332.3 R, 479 R

[56] References Cited

U.S. PATENT DOCUMENTS

| 2,214,117 | 9/1940 | Boese | 260/592 |
| 2,307,891 | 1/1943 | Lieber | 260/592 |

OTHER PUBLICATIONS

Olah, et al., J. Org. Chem., vol. 26, pp. 225-227, (1961).
Olah, (II), Freedel-Crafts & Related Reactions, vol. 1, pp. 317-321, (1963).
Simons, et al., J.A.C.S., vol. 61, pp. 1795-1796, (1939).

Primary Examiner—Bernard Helfin
Assistant Examiner—James H. Reamer
Attorney, Agent, or Firm—Curtis, Morris & Safford

[57] ABSTRACT

Aromatic 1,3-diketones are produced by reacting aromatic compounds with acetoacetyl fluoride optionally substituted in the γ-position by fluorine, chlorine and/or bromine, in hydrofluoric acid of at least 90% strength at a temperature of from about −40° to +50° C. The products obtained are important starting products and intermediates for the manufacture of dyestuffs, plastics and pharmaceuticals. Furthermore they can be used for the formation of metal complexes and as metal extracting agents, solution intermediaries and solvents.

12 Claims, No Drawings

PROCESS FOR THE MANUFACTURE OF AROMATIC 1,3-DIKETONES

This is a division of application Ser. No. 491,476, filed July 22, 1974 now U.S. Pat. No. 3,937,737.

This invention relates to a process for the manufacture of aromatic 1,3-diketones.

It is known to react benzene and benzene derivatives, for example toluene, o-, m-, and p-xylene, chlorobenzene and diphenyl ether, with diketene in the presence of 2 mols of aluminum chloride at a temperature of up to 60° C, whereby the corresponding acetoacetyl-aromatic compounds are obtained (cf. U.S. Pat. No. 2,214,117, and R. R. Estes and A. Tockman "Transactions of the Kentucky Academy of Science," 13, page 265 (1952)). In all relevant examples exclusively liquid benzene derivatives are used in a high excess as starting material, and simultaneously they have the function of a solvent in order that the mixtures can be stirred. The 1-arylbutane-1,3-diones obtained mostly form with the aluminum chloride, of which 2 mols must be used for each mol of diketene, complexes which are so stable that desired compounds can only be obtained therefrom by boiling them for several hours in dilute acids. In this process the used aluminum chloride is lost.

In the reaction of diketene with aromatic compounds that are solid at room temperature, for example acenaphthene, pyrene, or 2,6-dimethoxynaphthalene, solvents have to be added which do not react with diketene. The aforesaid literature references do not contain any description of corresponding experimentes. In proper experiments with 1,2-dichloroethane it has been found that with acenaphthene the yield is drastically reduced and resinifications do occur and that the aluminum chloride-butanedione complexes with pyrene have a high stability. If, however, the diketene is transformed into acetoacetyl fluoride which is then reacted with toluene in the presence of aluminum chloride in chloroform, a yield of only 6.5% of 1-tolyl-butane-1,3-dione is obtained, calculated on the diketene (cf. G. A. Olah and S. J. Kuhn, J, Org. Chem. 26, page 225 (1961)).

The present invention provides a process for the manufacture of a series of aromatic 1,3-diketones in good to very good yields by reacting acetoacetyl fluoride optionally carrying in the $\gamma$-position up to 3 identical or different halogen atoms selected from the group consisting of fluorine, chlorine and bromine with solid or liquid aromatic compounds in hydrofluoric acid of at least 90% strength, at a temperature of from about $-40°$ C to $+50°$ C, preferably about $-30°$ C to $+20°$ C. The optimum temperature range slightly varies and depends on the constitution of the compounds used. With compounds having free peri-positions, such as acenaphthene or pyrene, which may form a ring (cf. DOS Nos. 2,209,692, 2,262,857 and 2,262,858) the temperature should be in the range of from about $-40°$ to $-10°$ C, preferably $-30°$ to $-20°$ C, whereas compounds without free peri-positions are advantageously reacted at a temperature of about $-30°$ to $+20°$ C, preferably about $-20°$ to $+20°$ C. When operating within the aforesaid temperature range the reaction can be carried out without using special pressure resistant vessels. The vessels used are preferably made from polyethylene, polypropylene or polyvinyl chloride, or from metal, especially steel.

Owing to the fact that in the reaction no water is formed the hydrofluoric acid used can be substantially recovered by distillation. The same applies to the portion of unreacted aromatic compounds.

The reaction pressure largely corresponds to the inherent pressure of hydrofluoric acid which should have a minimum content of hydrogen fluoride of approximately 90% by weight, preferably 95 to 100% and more preferably about 98 to 100% by weight.

Depending on the reaction temperature the reaction time is in the range of from half an hour to several hours, i.e. at a reaction temperature below zero degree centigrade about 6 to 24 hours, at room temperature about 2 to 12 hours and at about 50° C, 30 to 120 minutes.

The process of the invention can be carried out, for example, in a manner such that the aromatic compound and the acetoacetyl fluoride are dissolved in hydrofluoric acid in approximately molar proportion at a temperature expediently below 0° C, preferably about $-30°$ C and the reaction mixture is heated to the desired reaction temperature, preferably with stirring.

It is possible to use an excess of acetoacetyl fluoride although this is hardly necessary. However, for a better utilization of the fluoride the aromatic compound may be used in an excess (about 1 to 5 mols). The aromatic compound does not undergo secondary reactions so that the unreacted portion thereof can be recovered by known methods and used again in the reaction.

The hydrofluoric acid is used in an amount of from about 1 to 20 parts by weight for 1 part of aromatic compound, preferably about 3 to 10 parts by weight. The reactants can be added in any order of succession, preferably one or both may be added in continuous manner. Alternatively, the whole process can be carried out continuously in simple manner by feeding all three components uniformly to a reaction vessel or tube. Instead of acetoacetyl fluoride the analogous chloride or bromide may be used. Such chloride or bromide reacts with the hydrofluoric acid to the fluoride.

The aforesaid acetoacetyl halides may be substituted in the $\gamma$-position by up to 3 halogen atoms, preferably chlorine, bromine and/or fluorine. The acetoacetyl halides substituted in the $\gamma$-position by halogen atoms can be prepared by known methods, for example as described in Houben-Weyl "Methoden der Organischen Chemie", volume 7/4, page 203, published by G. Thieme, Stuttgart (1968). Particularly suitable $\gamma$-halogen-substituted aceto-acetyl halides are $\gamma$-trifluoroacetoacetyl fluoride, $\gamma$-trichloro-acetoacetyl chloride, $ClF_2CCOCH_2COCl$, $Cl_2FCCOCH_2COCl$, $\gamma$-monochloro-acetoacetyl chloride, $\gamma$-mono-bromo-acetoacetyl bromide, or $\gamma$-dichloro-acetoacetyl chloride.

The compounds may additionally carry halogen atoms in the $\alpha$-position, although this is less preferable.

In a preferred variant of the process of the invention the unsubstituted acetoacetyl fluoride is produced in situ by adding diketene to hydrofluoric acid in excess (acetoacetyl fluoride from molar amounts of diketene and hydrogen fluoride of. G. A. Olah and S. J. Kuhn, J. Org. Chem. 26, page 225 (1961)) in the presence or absence of the aromatic compound, preferably at about $-40°$ to 0° C, and then reacting at the required temperature. In this mode of preparation of the acetoacetyl fluoride the excess of hydrofluoric acid is suitably so high that after the consumption of the acid to form the fluoride the amounts necessary for the reaction with the aromatic compound are still available.

When the reaction is terminated the hydrofluoric acid is suitably distilled off at atmospheric pressure and the residue is worked up by distillation. If the aromatic component contains free peri-positions, the hydrofluoric acid is distilled off under reduced pressure and at a temperature of the still of about −30° C to −40° C or below in order to avoid ring formation. The residue is worked up in known manner by recrystallizaion, column chromatography, or extraction of the desired compound with bases. Alternatively, the hydrofluoric acid solution obtained when the reaction is terminated can be introduced into water, whereupon the reaction products are filtered off with suction or extracted with halohydrocarbons.

Suitable aromatic compounds to be used in the process of the invention are, in principle, all condensed aromatics substituted or not at the ring system, for example naphthalene and its derivatives, also in the larger sense as obtained by substitution or condensation at the naphthalene ring and containing from 10 to 20 carbon atoms, preferably from 10 to 14 carbon atoms, such as the various alkyl or alkoxy-naphthalenes obtained by one- to three-fold, preferably one- to two-fold substitution of the naphthalene ring by alkyl and/or alkoxy groups having from 1 to 4, preferably 1 or 2, carbon atoms, advantageously the various methyl- and methoxy-naphthalenes. There are named by way of example 1-methyl-, 2-methyl-, 1-ethyl-, 2-ethyl-, 2,6-dimethyl-, 1,2,6-trimethyl-, 1-methoxy-, 2-methoxy-, 1-ethoxy-, 2-ethoxy-, 1,3-dimethoxy-, 1,6-diethoxy-, 1,8-dimethoxy-, 2,3-diethoxy-, 1,2,3-trimethoxy-, and 1,3,6-tributoxy-naphthalene.

Naphthalene derivatives with rings added by condensation which can be used in the process of the invention are, for example, anthracene, perylene, naphthacene or pyrene, as well as the corresponding mono-alkyl- or -alkoxy-compounds and corresponding polyalkylated or polyalkoxylated compounds.

Besides the aforesaid compounds, which will contain free peri-positions and are reacted in a low temperature range, substitution products of naphthalene in which the peri-position is blocked by a substituent may also be used, for example 1,4-dimethoxy- and 1,4-dimethyl-naphthalene.

Further suitable starting compounds are benzene derivatives of the formula

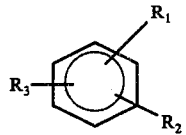

in which $R_1$, $R_2$, and $R_3$, independent of one another, represent hydrogen, $C_1$ - $C_{12}$, preferably $C_1$ - $C_6$ and more preferably $C_1$ - $C_4$, alkyl, alkoxy or alkylthio, one of the radicals also being optionally substituted phenyloxy or phenylthio, or halogen, preferably fluorine, chlorine or bromine. Suitable radicals are, for example $CH_3$, $C_2H_5$, $C_3H_7$, $C_4H_9$, $C_6H_{13}$, $OC_2H_5$, $OC_3H_7$, $OC_4H_9$, $S—CH_3$, $SC_2H_5$, $SC_3H_7$, $SC_4H_9$, $O—C_6H_5$, $O—CH_2—C_6H_5$ and $SC_6H_5$. In the case of one of the radicals $R_1$, $R_2$, or $R_3$ being halogen, those benzene derivatives are preferred in which at least one of the remaining radicals is alkyl, alkoxy, or alkylthio.

Still further aromatic compounds can be used in which two of the radicals $R_1$, $R_2$ and $R_3$ are linked to a ring or in which benzene derivatives, as specified above, are constituents of 5 or 6 membered heterocyclic rings, for example dibenzofurane or dibenzo-p-dioxan or compounds of the formula

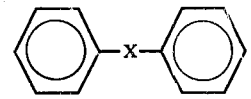

in which X is oxygen, sulfur or $(CH_2)_n$, $n$ being 1 to 4. Compounds having two benzene rings, for example diphenyl ether and the substitution products thereof, as specified above may be reacted twice. Further suitable starting compounds are thiophene and the mono-alkyl, dialkyl and benzo derivatives thereof.

When a substance is used which reacts with diketene only with difficulty or not at all, it may be advantageous to add a molar amount of a further substance having similar properties but being more reactive with regard to diketene. In this manner the reaction with the inactive substance can be induced. For example, by reacting a mixture of 1 mol of dodecyl-benzene and 1 mol of tetrahydronaphthalene with 2 mols of diketene in hydrochloric acid a yield of 40% of acetoacetyl-dodecylbenzene can be obtained which would be hardly possible without the addition of tetrahydronaphthalene.

Acetoacetyl-dodecyl-benzene and the compounds of the formula

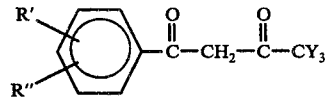

in which R' and R", independent of each other, are hydrogen or alkyl and the sum of carbon atoms in the radicals R' and R" is in the range of from 6 to 12 and Y represents hydrogen and/or fluorine, chlorine, or bromine are novel. Further novel compounds which can be prepared by the process of the invention, and which are of interest, are tetrahydronaphthalene acetoacetylized in the α- or β-position at the aromatic ring and the acetoacetylized isomeric diethyl-benzenes.

The compounds obtained by the process of the invention can be used as intermediate and final products, for example for the formation of metal complexes, as metal extracting agents, as dyestuff intermediates, as monomers for plastic materials, as intermediates for the production of plant protection agents and pharmaceuticals, and as dissolving intermediaries or solvents.

1-Aryl-butane-1,3-diones which can be prepared by the process of the invention are, for example, 1-acetoacetyl-2,6-dimethoxy-naphthalene, 4-acetoacetyl-diphenyl-sulfide, 2-chloro-and 2-bromo-4-acetoacetyl-anisole, 3-acetoacetyl-diphenylene oxide, 2,2'-dimethoxy-4,4'-bisacetoacetyl-diphenyl ether, 3-chloro-6-acetoacetyl-pyrene, 1-methyl-4-acetoacetyl-naphthalene, 3-acetoacetyl-pyrene and 1-methoxy-4-acetoacetyl-naphthalene.

The following examples illustrate the invention.

EXAMPLE 1

165.6 g (1.2 mols) of 1,2-dimethoxybenzene in 600 ml of anhydrous hydrofluoric acid were introduced, while stirring at −20° C, into a 1 liter polyethylene vessel and 108 ml (1.4 mols) of diketene were dropped in while further cooling. Stirring was continued for 4 hours while cooling with ice, the reaction mixture heated for 3 hours at room temperature and the hydrofluoric acid distilled off. The residue was washed to remove the acid and subjected to vacuum distillation, whereby the 1,2-dimethoxy-4-acetoacetyl-benzene passed over at a boiling point of 132° C under 0.05 torr, (mm.Hg) which solidified in the form of colorless crystals.
Yield: 219 g, i.e. 82.3% of the theory, calculated on the amount of 1,2-dimethoxy-benzene used.

EXAMPLE 2

150 ml of anhydrous hydrofluoric acid were introduced at −30° C into a steel vessel, 18 ml (0.23 mol) of diketene and then 21.2 g (0.2 mol) of m-xylene were added dropwise. The reaction mixture was allowed to warm up to room temperature. After 7 hours the hydrofluoric acid was distilled off while thoroughly stirring. The residue was washed until it was free from acid and by distillation were obtained ±g (92%, calculated on m-xylene) of a mixture boiling at 99° – 104°C and consisting according to the gas chromatogram of 96.9% of 1,3-dimethyl-4-acetoacetyl-benzene and 2.7% of 1,3-dimethyl-2-acetoacetyl-benzene.

EXAMPLE 3

In an autoclave 27 ml (0.35 mol) of diketene were added dropwise at −30° C to 150 ml of anhydrous hydrofluoric acid and then 31.8 g (0.3 mol) of o-xylene were added. After 4 hours stirring at room temperature, the mixture was heated for 30 minutes to 50° C. After distillation of the hydrofluoric acid and washing out of the residual acid, 44 g (78%, calculated on o-xylene) of a mixture passed over at 110° – 115° C under 0.6 torr, which consisted of 92% of 1,2-dimethyl-4-acetoacetyl-benzene and 7% of 1,2-dimethyl-6-acetoacetyl-benzene according to the gas chromatogram.

Using p-xylene, 1,4-dimethyl-2-acetoacetyl-benzene distilling over at 99° C under 0.7 torr was obtained in analogous manner in a yield of 67%

EXAMPLE 4

54 ml (0.7 mol) of diketene were added dropwise at 0° C to 72 g (0.6 mol) of mesitylene in 500 ml of anhydrous hydrofluoric acid and after 6 hours stirring at room temperature the reaction mixture was stirred into 3 l of water. After standing overnight 115 g (94% calculated on mesitylene) of colorless crystals of acetoacetyl-mesitylene melting at 41° C separated, which were found to be uniform by thin layer chromatography.

EXAMPLES 5 to 21

The reaction was carried out as described in Example 2. The results are summarized in the following table.

| Example No. | starting compound (A) | mol diketene per mole of A | final product | yield (%) | melting point ° C or boiling point ° C/torr |
|---|---|---|---|---|---|
| 5 | 2-chloroanisole | 1 | 4-acetoacetyl-2-chloroanisole | 79 | 129 |
| 6 | 2-bromoanisole | 1 | 4-acetoacetyl-2-bromoanisole | 63 | 123 |
| 7 | diphenyleneoxide | 1 | 3-acetoacetyl-diphenylene oxide | 74 | 125 |
| 8 | diphenyl ether | 1 | 4-acetoacetyl-diphenyl ether | 59 | 80 |
| 9 | diphenyl ether | 2 | 4-4'-bis-acetoacetyl-diphenyl-ether besides | 19 | 152 |
|   |   |   | 4-acetoacetyl-diphenyl ether | 39 |   |
| 10 | 2,2'-dimethoxy-diphenyl ether | 2 | 4,4'-bis-acetoacetyl-2,2'-dimethoxy-diphenyl ether | 43 | 142 |
| 11 | diphenyl sulfide | 1 | 4-acetoacetyl-diphenyl sulfide | 39 | 75 |
| 12 | 4-methylanisole | 1 | 2-acetoacetyl-4-methylanisole | 81 | 115/0.1 torr |
| 13 | anisole | 1 | 4-acetoacetyl-anisole | 71 | 54 |
|   |   |   | 2-acetoacetyl anisole | 12 | 36 |
| 14 | toluene | 1 | hexyltoluene toluene | 80 |   |
|   |   |   |   |   | 110/0.9 torr |
|   |   |   | 2-acetoacetyl-toluene | 7 |   |
| 15 | p-Xylene | 1 | 1,4-dimethyl-2-acetoacetyl-benzene | 69 | 99/0.7 torr |
| 16 | m-hexyltoluene | 1 | acetoacetyl-+) hexyltoluene | 63 | 135–145/ 1.5 torr |
| 17 | tetrahydro-naphthalene | 1 | acetoacetyl-+) tetrahydro-naphthalene | 79 | 160–165/ 1.5 torr |
| 18 | di-isopropyl-benzene+) | 1 | acetoacetyl-+) di-isopropyl-benzene | 61 | 140/1.5 torr |
| 19 | diethyl-benzene+) | 1 | acetoacetyl-+) di-ethyl-benzene | 59 | 120–138/ 0.6 torr |
| 20 | thiophene | 1 | 2-acetoacetyl-thiophene | 67 | 32 |
| 21 | cumene | 1 | 4-acetoacetyl-cumene | 75 | 120/2 torr |

EXAMPLE 22

33.6 g (0.4 mol) of diketene were added drop by drop, while stirring at −30° C, to 37.6 g (0.2 mol) of 2,6-dimethoxynaphthalene in 200 ml of anhydrous hydrofluoric acid and the mixture was stirred for another 8 hours at said temperature. The hydrogen fluoride was distilled off under reduced pressure at a temperature of the still of −30° C and the residue washed until it was free from acid. After sublimation of unreacted starting product (11 g = 71% conversion) colorless crystals of 1-acetoacetyl-2,6-dimethoxynaphthalene melting at 88° C were obtained by column chromatography (silica gel, 0.065 - 0.2 mm, CH$_2$Cl$_2$) in an amount of 35 g (90% calculated on 2,6-dimethoxynaphthalene).

EXAMPLE 23

42 g (0.5 mol) of diketene were added dropwise to 77 g of acenaphthene (0.5 mol) in 300 mol of anhydrous hydrofluoric acid at −30° C while stirring. The temperature was maintained for 9 hours. The hydofluoric acid was distilled off under reduced pressure at a temperature of the still of −30° C, the residue was washed until it was free from acid and distilled under reduced pressure. 10 g of unreacted acenaphthene were recovered (87% conversion). At a transition temperature of 150° -155° C under 0.4 torr 85 g (82% of theory) of slightly yellowish 5-acetoacetyl-acenaphthene melting at 59° C were then obtained.

EXAMPLE 24

42 g (0.5 mol) of diketene were added dropwise at −40° C to 79 g (0.5 mol) of 2-methoxy-naphthalene in 300 ml of anhydrous hydrofluoric acid, stirring was continued for 7 hours at −25° to −35° C and the reaction mixture was stirred into 3 l of water. After extraction with methylene chloride, drying and eliminating the solvent, the residue was distilled. First 12 g of methoxy-naphthalene were recovered at 95°C/0.5 torr (84.5% conversion) and then 90 g (86.5%) of 1-acetoacetyl-2-methoxynaphthalene melting at 77° C (recrystallized from ethanol) passed over at 163° C/0.8 torr.

EXAMPLES 25 and 26

The reaction was carried out as described in Example 24. The result is summarized in the following table:

| Ex. No. | starting compound (A) | mol diketene per mol of A | final product | yield (%) | melting p. ° C or boiling p. ° C/torr |
|---|---|---|---|---|---|
| 25 | 1-methoxy-naphthalene | 1 | 1-methoxy-4-acetoacetyl-naphthalene | 77 | 178/0.3 torr |
| 26 | 1-methyl-naphthalene | 1 | 1-methyl-4-acetoacetyl-naphthalene | 89 | 145/0.3 torr |

EXAMPLE 27

100.8 g (1.2 mols) of diketene were dropped at −20° C into 500 ml of anhydrous hydrofluoric acid and at the same temperature 242.4 g (1.2 mols) of pyrene were added in portions, whereupon the mixture was stirred for 16 hours at −15° to −10° C. After distillation of the hydrofluoric acid at a temperature of the still of −15° C at reduced pressure, the residue was taken up in methylene chloride, washed with water and dried over sodium sulfate. After elimination of the solvent, 307 g of yellow crystals of 3-acetoacetyl-pyrene were obtained, corresponding to a yield of 89%.

After recrystallization from cyclohexane, the yellow crystals obtained melted at 86° -88° C.

EXAMPLE 28

In the manner described in Example 27 3-chloro-6-acetoacetyl-pyrene melting at 105° C was obtained in a 71% yield from 3-chloropyrene.

EXAMPLE 29

The following compounds
2-methyl-1-acetoacetyl-naphthalene
2,7-dimethoxy-1-acetoacetyl-naphthalene and
3-acetoacetyl-perylene
were prepared in the manner described in Example 24. Furthermore
1,4-dimethyl-5-acetoacetyl-naphthalene and
1,4-dimethoxy-5-acetoacetyl-naphthalene
were prepared as described in Example 2.

Example 30

100.8 g (1.2 mols) of diketene were added dropwise at −30° C to 0.5 l of anhydrous hydrofluoric acid and a mixture of 0.6 mol of tetrahydronaphthalene and 0.6 mol of commercial grade dodecyl-benzene were dropped in. After stirring for 12 hours at room temperature, the reaction mixture was stirred into 3 l of icewater. After extraction with methylene chloride, washing with water to remove the acid from the organic phase and distillation of the methylene chloride, distillation of the reaction mixture yielded 86% of acetoacetyl-tetrahydronaphthalene boiling at 135° C under 0.5 terr and 77 g ($\triangleq$ 40%) of acetoacetyl-dodecyl-benzene boiling at 160° C under 0.5 torr as found by gas chromatographic determination of the fractions.

EXAMPLE 31

Crude γ-trichloro-acetoacetyl chloride, prepared from 0.5 mol each of trichloroacetyl chloride and ketene (cf. Houben-Weyl, loc. cit) was carefully freed from the solvent and dropped at -20° C while stirring into 0.5 l of hydrofluoric acid. Next, 0.5 mol of m-xylene was added, the reaction mixture was stirred for 10 hours at room temperature, poured into icewater and extracted with methylene chloride.

After distillation 79 g of light yellow, liquid 1-γ-trichloroacetoacetyl-2,4-dimethyl-benzene were obtained which had a strength of 94.5% according to gas chromatography. The theoretical yield over two stages was 50.5% and the boiling point was 166° C under 2 - 3 torr.

EXAMPLE 32

The reaction was carried out in a manner analogous to Example 31 with γ-trifluoroaetoacetyl-chloride and mesitylene in hydrofluoric acid. 1-γ-trifluoroacetoacetyl-2,4,6-trimethylbenzene was obtained as a light yellow liquid boiling at 80°-82° C under 0.8 torr.

EXAMPLE 33

0.5 mol of γ-chloroacetoacetyl chloride (as crude product after removal of solvent, cf. Houben-Weyl loc. cit, pages 252/2) and 0.5 mol of 2-anisyl-chloroacetic acid ester were introduced at −10° C into 0.5 l of hydrofluoric acid and stirring was continued for 8 hours at 15° C.

By pouring the reaction mixture into icewater, extraction and column chromatography (silica gel 0.05 -0.2 mm, CH$_2$Cl$_2$) colorless crystals of 3-γ- chloroacetoacetyl-6-methyl-chloroacetic acid phenyl ester melting at 107° C were obtained.

EXAMPLE 34

When toluene was used 4-γ-chloroacetoacetyl-toluene was obtained in analogous manner as a light brown, readily decomposable liquid having a refractive index $n_D^{23}$ of 1.6008 in a yield of 30% (over two stages, calculated on the diketene used.

EXAMPLE 35

When crude γ-bromoacetoacetyl bromide (literature cf. Example 33) and mesitylene were reacted in analogous manner, γ-bromoacetoacetyl mesitylene was obtained as a brown readily decomposable liquid which was characterized by nuclear magnetic resonance spectrum as follows:

| NMR (CDCl₃, TMS, δ) | | | |
|---|---|---|---|
| | 2.32 ppm | 3 × CH₃ | (s) |
| | 3.90 ppm | -CH₂Cl | (s) |
| | 5.90 ppm | —CH = | (s) |
| | 6.84 ppm | 2 arom. H | (s) |
| | 14.00 ppm | enol-H | (s) |

EXAMPLE 36

When toluene was used in a manner analogous to that of the preceding example and the reaction mixture was worked up in a chromatographic column 1-p-tolyl-4-bromo-butane-dione-1,3 was obtained in the form of light pink cyrstals melting at 52° C.

What is claimed is:

1. A process for the preparation of an aromatic 1,3-diketone which comprises reacting acetoacetylfluoride, or an acetoacetylfluoride substituted at the gamma-position by up to three halogens selected from the group consisting of fluorine, chlorine and bromine, with an aromatic compound selected from the group consisting of naphthalene; naphthalene substituted by up to three substituents selected from the group consisting of alkyl of from 1 to 4 carbon atoms and alkoxy of from 1 to 4 carbon atoms; naphthalene with one or more condensed rings thereon having in total up to 20 carbon atoms; naphthalene with one or more condensed rings thereon and substituted by up to three sustituents selected from the group consisting of alkyl of 1 of 4 carbon atoms and alkoxy of from 1 to 4 carbon atoms, having in total up to 20 carbon atoms; benzene of the formula

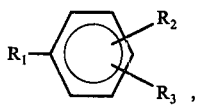

wherein R₁, R₂ and R₃ each is hydrogen, alkyl of up to 12 carbon atoms, alkoxy of up to 12 atoms, alkylthio of up to 12 carbon atoms or benzyloxy or R₁ is phenyloxy, substituted phenyloxy, phenylthio, substituted phenylthio or halogen, or wherein R₁ and R₂ together form alkylene of 4 carbon atoms; diphenyl of the formula

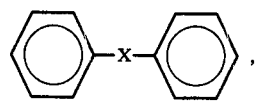

wherein X is O, S or alkylene of up to 4 carbon atoms; dibenzofurane; dibenzo-p-dioxane; thiophene; monoalkylthiophene; dialkylthiophene; benzothiophene; 2,2′-dimethoxy diphenyl ether; 3-chloro-pyrene; and 2-anisyl-chloracetic acid ester, at a temperature of about −30°C. to about +20° C. in the presence of anhydrous hydrogen fluoride or hydrofluoric acid having a minimum amount of hydrogen fluoride of about 90% by weight.

2. The process as defined in claim 1, wherein the aromatic compound is selected from the group consisting of naphthalene substituted by up to three substituents selected from the group consisting of alkyl of from 1 to 4 carbon atoms and alkoxy of 1 to 4 carbon atoms; naphthalene with one or more condensed rings thereon having in total up to 20 carbon atoms; enzene of the formula

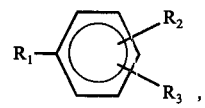

wherein R₁, R₂ and R₃ each is hydrogen, alkyl of up to 12 carbon atoms, or alkoxy of up to 12 carbon atoms, or R₁ is halogen; or wherein R₁ and R₂ together form alkylene of 4 carbon atoms; diphenyl of the formula

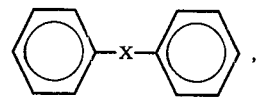

wherein X is oxygen or sulfur; dibenzofurane, thiophene; 2,2′-dimethoxy diphenyl ether; 3-chloro-pyrene; and 2-anisyl-chloroacetic acid ester.

3. The process as defined in claim 1 wherein the naphthalene with one or more condensed rings thereon is acenaphthene, anthracene, perylene, naphthacene or pyrene.

4. A process as defined in claim 1 wherein the substituted naphthalene is 1-methyl-, 2-methyl-, 1-ethyl-, 2-ethyl-,2,6-dimethyl-, 1,4-dimethyl-, 1,2,6-trimethyl-, 1-methoxy-,2-methoxy-, 1-ethoxy-, 2-ethoxy-, 1,3-dimethoxy-, 1,4-dimethoxy-, 1,6-diethoxy-, 1,8-dimethoxy-, 2,3-diethoxy-, 1,2,3-trimethoxy- or 1,3,6-tributoxy-naphthalene.

5. A process as defined in claim 1 wherein said alkyl, alkoxy and alkylthio of R₁, R₂ and R₃ have up to 4 carbon atoms.

6. A process as defined in claim 1 wherein said R₁, R₂ and R₃ each is —H, —CH₃, —C₂H₅, —C₄H₉, —C₆H₁₃, —OC₂H₅, —OC₃H₇, —SC₄H₉, —SCH₃, —SC₂H₅, —SC₃H₇, —SC₄H₉ or —OCH₂—C₆H₅ or R₁ is —OC₆H₅ or —SC₆H₅.

7. A process according to claim 1 wherein the amount of hydrogen fluoride is at least about 95%.

8. A process according to claim 1 wherein the reaction occurs during a period of about one-half to about 24 hours.

9. A process according to claim 1 wherein about 1 to about 5 mols of said aromatic compound are used per mol of said acetoaetylfluoride.

10. A process according to claim 1 wherein said hydrofluoric acid is used in an amount of about 1 to about 20 parts by weight per part of said aromatic compound.

11. A process according to claim 1 wherein said hydrofluoric acid is used in an amount of about 3 to about 10 parts by weight per part of said aromatic compound.

12. A process according to claim 1 wherein acetoacetylfluoride is produced in situ by adding diketene to an excess of said hydrofluoric acid at a temperature of about −40° C. to about 0° C.

* * * * *